US010359443B2

(12) United States Patent
Wan et al.

(10) Patent No.: US 10,359,443 B2
(45) Date of Patent: Jul. 23, 2019

(54) FULLY AUTOMATIC FECAL OCCOULT BLOOD DETECTING ANALYZER

(71) Applicant: W.H.P.M. BIORESEARCH AND TECHNOLOGY CO., LTD., Beijing (CN)

(72) Inventors: John Wan, Beijing (CN); Chunhai Zou, Beijing (CN); Qinghai Xia, Beijing (CN); Jie Liu, Beijing (CN)

(73) Assignee: W.H.P.M. BIORESEARCH AND TECHNOLOGY CO., LTD., Beijing (CN)

( * ) Notice: Subject to any disclaimer, the term of this patent is extended or adjusted under 35 U.S.C. 154(b) by 85 days.

(21) Appl. No.: 15/538,521

(22) PCT Filed: Dec. 24, 2015

(86) PCT No.: PCT/CN2015/098745
§ 371 (c)(1),
(2) Date: Jun. 21, 2017

(87) PCT Pub. No.: WO2016/107495
PCT Pub. Date: Jul. 7, 2016

(65) Prior Publication Data
US 2018/0031590 A1 Feb. 1, 2018

(30) Foreign Application Priority Data

Dec. 31, 2014 (CN) .......................... 2014 1 0852473

(51) Int. Cl.
*G01N 35/00* (2006.01)
*G01N 35/04* (2006.01)
(Continued)

(52) U.S. Cl.
CPC ......... *G01N 35/04* (2013.01); *A61B 10/0038* (2013.01); *G01N 33/4833* (2013.01);
(Continued)

(58) Field of Classification Search
CPC ....... B01L 2400/0683; B01L 2300/046; G01N 33/72; G01N 35/00029; G01N 2035/0406;
(Continued)

(56) References Cited

U.S. PATENT DOCUMENTS 4,039,287 A 8/1977 Moran
4,268,477 A 5/1981 Herzstark
(Continued)

FOREIGN PATENT DOCUMENTS

CN 1875280 A 12/2006
CN 101949947 A 1/2011
(Continued)

OTHER PUBLICATIONS

International Search Report issued in International Application No. PCT/CN2015/098745 dated Mar. 21, 2016.

*Primary Examiner* — Harshad R Patel
*Assistant Examiner* — Brandi N Hopkins
(74) *Attorney, Agent, or Firm* — Scully Scott Murphy & Presser

(57) ABSTRACT

An automatic fecal occult blood detecting analyzer used to detect a sample box is provided. The analyzer has a feeding chain and a main conveying chain. A plurality of clamping devices for clamping the sample box are provided on the feeding chain and the main conveying chain, respectively. A transferring device of the analyzer transfers the sample box from the feeding chain to the main conveying chain. The analyzer also has a pressing device and an image acquisition device for acquiring tape information presented on test strips of the sample box on the main conveying chain. Continuous detection and accurate location of a plurality of the sample boxes can be implemented without turning over and tilting the sample boxes.

10 Claims, 5 Drawing Sheets

(51) Int. Cl.
*A61B 10/00* (2006.01)
*G01N 33/483* (2006.01)

(52) U.S. Cl.
CPC .............. *G01N 35/00584* (2013.01); *G01N 2035/0439* (2013.01); *G01N 2035/0493* (2013.01)

(58) Field of Classification Search
CPC ......... G01N 2035/00128; G01N 35/04; G01N 35/021; G01N 2035/0429; G01N 2035/0484; G01N 2035/00089; G01N 35/02; A61B 10/0038
See application file for complete search history.

(56) References Cited

U.S. PATENT DOCUMENTS

| | | | | |
|---|---|---|---|---|
| 5,324,479 | A * | 6/1994 | Naldoni | B01F 13/0818 |
| | | | | 422/63 |
| 8,262,994 | B2 * | 9/2012 | Hamada | G01N 35/026 |
| | | | | 422/63 |
| 2007/0110617 | A1 * | 5/2007 | Nagai | G01N 35/026 |
| | | | | 422/65 |
| 2016/0266150 | A1 * | 9/2016 | Wan | A61B 10/0038 |
| 2016/0334426 | A1 * | 11/2016 | Li | G01N 33/483 |

FOREIGN PATENT DOCUMENTS

| | | |
|---|---|---|
| CN | 103543285 A | 1/2014 |
| CN | 203519625 U | 4/2014 |
| CN | 104569460 A | 4/2015 |
| EP | 1 460 428 A1 | 9/2004 |

* cited by examiner

FULLY AUTOMATIC FECAL OCCOULT BLOOD DETECTING ANALYZER

TECHNICAL FIELD OF THE INVENTION

The present invention relates to the field of medical detection, and particularly to a fully automatic fecal occult blood detecting analyzer, namely a fully automatic FOB detecting analyzer.

BACKGROUND OF THE INVENTION

"FOB": the abbreviation of English is fecal occult blood, refers to occult blood in feces, be called fecal occult blood for short, which is slight hemorrhage of the digestive tract. Generally, fecal occult blood does not cause a change in feces color. Erythrocytes are damaged by digestion and there is no abnormal change in feces appearance. Bleeding cannot be confirmed visibly and microscopically. A small amount of blood cells in feces can be discovered only when the feces are tested. A small amount of bleeding for a long time is usually accompanied by anaemic symptom. Since fecal occult blood cannot be discovered directly through eyes, most patients suffering from malignant tumors of the digestive tract at early stages cannot be diagnosed in time and fail to receive early intervening treatment, thus missing the best time for treatment, and fecal occult blood ambushes in people's bodies like a silent killer.

Fecal occult blood are mostly detected through a feces collector matched with a casse in the prior art. After a fecal sample of a patient is collected, a diluent with the fecal sample is dripped into a sample dripping hole of the casse and a detection result is observed. Such operation results in a low efficiency for mass detection. Besides, the diluent with the fecal sample is exposed in the air to form an odor, which pollutes the environment.

CN103543285A discloses an automatic fecal occult blood detection device for detecting a sample box. The sample box includes a transparent sleeve, and a feces collector and test strips provided in the transparent sleeve. The detection device includes: a import channel and a export channel are provided in coordination and respectively configured to independently operate for conveying a sample box; a transferring platform is located between the import channel and the export channel; a push rod is configured to push the sample box on the import channel to the export channel by the transferring platform, and an image acquisition device is provided at one side of the export channel, wherein the image acquisition device is configured to acquire colored tape information presented on the test strips.

The automatic fecal occult blood detection device has the following problems:

The import channel and the export channel are provided in coordination, which increases a floor space of the device.

Sample boxes are placed randomly on the import channel and the export channel at disordered intervals, sample boxes on the import channel, the export channel and the transferring platform are easy to topple, thus it is possible to affect detection of subsequent sample boxes, and the device needs to be shut down for inspection in a severe case.

An action of the push rod may overturn a sample box easily, and the foregoing problem also exists. A sample box can be hardly pressed well when a pressing member acts, thus detection cannot be performed. Or the sample box may be overturned when the pressing member acts, and subsequent image acquisition cannot be completed. A push plate mechanism of the device also has the foregoing problems.

In addition, the device requires shaking up a fecal sample in a sample box manually, which increases labour and reduces the detection efficiency.

To sum up, the prior art at least has the following problem that a sample box is be overturned or toppled easily during a detection process.

SUMMARY OF THE INVENTION

The present invention provides a fully automatic fecal occult blood detecting analyzer to solve a problem that a sample box is overturned or toppled easily during a detection process.

For this purpose, the present invention provides a fully automatic fecal occult blood detecting analyzer used to detect a sample box. The sample box comprises a transparent sleeve and a feces collector and test strips provided in the transparent sleeve. The fully automatic fecal occult blood detecting analyzer comprises: a feeding chain and a main conveying chain; a plurality of clamping devices for clamping the sample boxes are respectively provided on the feeding chain and the main conveying chain; a transferring device is provided in an areas confined by the main conveying chain; a pressing device is configured to press the feces collector during a moving process of the sample box and provided above the main conveying chain; an image acquisition device is configured to acquire colored tape information presented on the test strips in the sample box on the main conveying chain.

Further, both the feeding chain and the main conveying chain are located in one horizontal plane; the clamping devices are installed on laterals of the feeding chain and the main conveying chain; the sample box is clamped vertically in the clamping devices; a side face of the sample box is clamped by side faces of the clamping devices.

Further, the clamping devices are elastic clamping devices made of elastic materials, and the elastic clamping devices comprise: open slots formed by the elastic materials, openings of the open slots are located in a vertical plane.

Further, the transferring device comprises: a pull rod is capable of moving between the feeding chain and the main conveying chain, and a transferring supporting platform is located between the feeding chain and the main conveying chain; the transferring supporting platform supports the sample box.

Further, the pull rod comprises: an upper pull rod and a lower pull rod located below the upper pull rod; the upper pull rod is in a horizontally-provided L shape; a plane where the upper pull rod locates is higher than the top surfaces of the feeding chain and the main conveying chain; the lower pull rod comprises: a horizontally-provided traverse rod and a vertical rod connected to an end of the traverse rod; the vertical rod is provided vertical to the traverse rod; the traverse rod is lower than the bottom surfaces of the feeding chain and the main conveying chain; the top surface of the vertical rod is lower than the plane where the upper pull rod locates; an opening for moving the vertical rod is provided in the transferring supporting platform; the width of the opening is smaller than that of the sample box; the lower pull rod is capable of extending from the bottom of the transferring supporting platform into the feeding chain.

Further, the fully automatic fecal occult blood detecting analyzer further comprises: a discharging device is used for sending the sample box out from the main conveying chain.

Further, the fully automatic fecal occult blood detecting analyzer further comprises: a waste supporting platform is used for supporting the sample box sent out by the discharging device; the waste supporting platform is located between the feeding chain and the main conveying chain, and the waste supporting platform and the transferring supporting platform are located on the same plane; the longitudinal width of the waste supporting platform is smaller than the length of a long side of the sample box.

Further, the fully automatic fecal occult blood detecting analyzer further comprises: a waste discharging device is used for pushing the sample box away from the waste supporting platform.

Further, the fully automatic fecal occult blood detecting analyzer further comprises: a stepping motor is used for driving the feeding chain to move and vibrating the sample box.

Further, the fully automatic fecal occult blood detecting analyzer further comprises: a recycling device is configured to recycle the sample box and located at a terminal end of the waste supporting platform; a machine shell is configured to enclose the feeding chain, the main conveying chain, a driving wheel of the feeding chain, a driving wheel of the main conveying chain, and the clamping devices; a feed inlet port is provided on the machine shell and communicating with the feeding chain; a protection cover is provided on the machine shell and located at the feed inlet port; a flange is provided at one or two sides of the machine shell above the waste supporting platform.

The present invention arranges the clamping devices on the feeding chain and the main conveying chain so that the sample box can be well clamped during a detection process. The sample box can be limited and clamped by the clamping devices no matter during a transferring process, or during a process of pressing the sample box and detecting the feces collector, thus solving problems of overturning and toppling. Preferably, the clamping devices are elastic clamping devices made of elastic materials, thus adapting to feces collectors of various models.

Further, a feeding channel and a main conveying channel for detecting and conveying the sample box of the present invention apply chain conveying structures in order to combine a conveying process and a clamping process of the sample box organically. In this way, the clamping devices can well clamp the sample box without affecting conveyance, thus matching conveying and clamping organically.

DETAILED DESCRIPTION OF THE EMBODIMENTS

Figure 7:
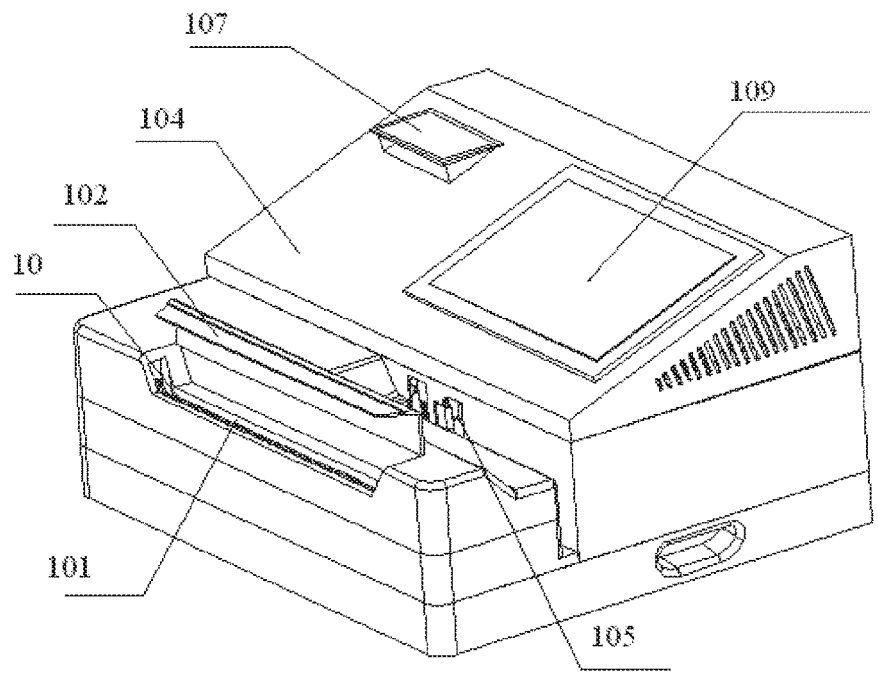
Figure 8:
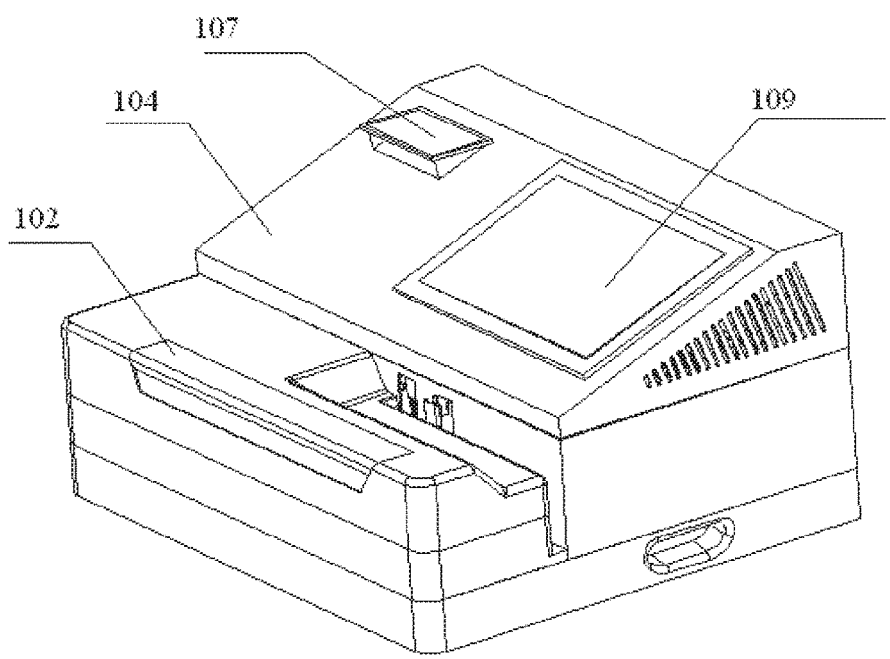

FIG. 7 is a schematic diagram of an external structure of a fully automatic fecal occult blood detecting analyzer according to an embodiment of the present invention, wherein a feed inlet port is in an open state; and FIG. 8 is a schematic diagram of an external structure of a fully automatic fecal occult blood detecting analyzer according to an embodiment of the present invention, wherein a feed inlet port is in a closed state.

NUMERALS IN THE ACCOMPANYING DRAWINGS

10: Feeding chain; 11: Driving wheel of feeding chain; 15: Feeding track; 20: Main conveying chain; 21: Driving wheel of main conveying chain; 30: Sample box; 40: Clamping device; 50: Pull rod; 51: Upper pull rod; 52: Lower pull rod; 520: Traverse rod; 522: Vertical rod; 53: Transferring supporting platform; 55: Open hole; 60: Discharging device; 70: Waste discharging device; 71: Waste supporting platform; 80: Camera device; 81: First sensor; 82: Second sensor; 83: Third sensor; 84: Fourth sensor; 85: Fifth sensor; 88: Barcode scanning device; 90: Pressing device; 101: Feed inlet port; 102: Protection cover; 104: Machine shell; 105: Discharging port; 107: Printing device; 109: Control panel; 301: Open slot

DETAILED DESCRIPTION OF THE EMBODIMENTS

The present invention will be described with reference to the accompanying drawings in order to understand the technical features, purposes, and effect of the present invention more clearly.

Figure 1:
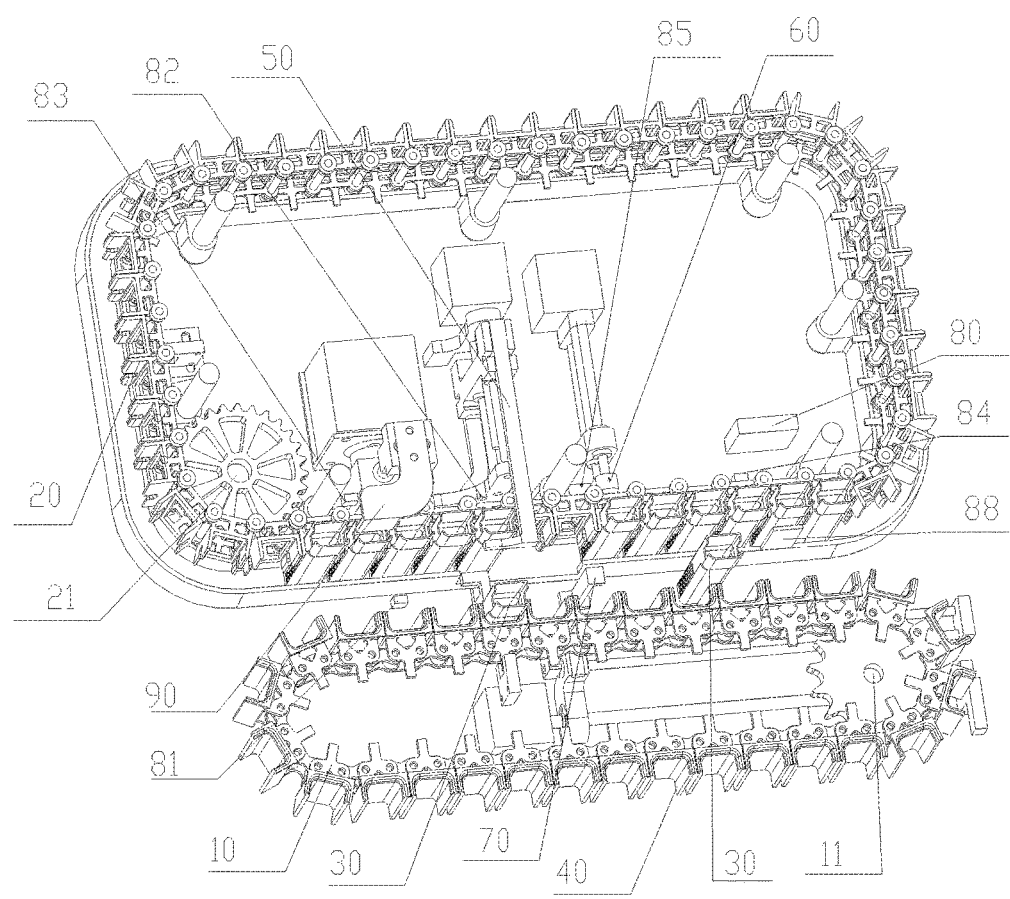
FIG. 1 is a schematic diagram of an internal structure of a fully automatic fecal occult blood detecting analyzer according to an embodiment of the present invention.

As shown in FIG. 1, the present invention provides a fully automatic fecal occult blood detecting analyzer used to detect a sample box 30. The sample box comprises a transparent sleeve and a feces collector and test strips provided in the transparent sleeve. A specific structure of the sample box may refer to a structure in the Chinese patent document 103543285.

The fully automatic fecal occult blood detecting analyzer comprises:

A feeding chain 10 and a main conveying chain 20 are annular. The main conveying chain 20 is located at one side of the feeding chain 10 and the two are exclusive to each other so that they are independent respectively. As a preferred option, the feeding chain 10 and the main conveying chain 20 are closed annular chains in various shapes, comprising rectangles or approximate rectangles, circles or approximate circles, as long as the shapes of the feeding chain 10 and the main conveying chain 20 can be placed in a machine shell 104. The feeding chain 10 is connected to a driving wheel of the feeding chain 11 and the main conveying chain 20 is connected to a driving wheel of the main conveying chain 21. Chain conveying may prevent overturning and implement accurate location. In addition, chain conveying has higher efficiency in the case that the length and width of the whole detecting analyzer are fixed.

A plurality of clamping devices 40 for clamping the sample box are respectively provided on the feeding chain 10 and the main conveying chain 20. Since the feeding chain 10 and the main conveying chain 20 are chain structures the feeding chain 10 and the main conveying chain 20 may be formed by a plurality of chain units, each of which may be installed with one clamping device 40 thereon for clamping the sample box 30. The clamping devices 40 on the feeding chain 10 clamp the sample box 30 during a feeding process and the clamping devices 40 on the main conveying chain 20 clamp the sample box 30 during detection, so that the sample box 30 can be limited and clamped by the clamping devices 40 no matter during feeding, transferring, pressing, or during subsequent detection, acquisition of patient information, and a photograph process of a detection result, thus solving problems of overturning and toppling, and implementing accurate location. The clamping devices 40 may be made of rubber or other elastic materials, thereby adapting to feces collectors of various models.

A transferring device is provided in an areas confined by the main conveying chain 20 and configured to transfer the sample box 30 from the feeding chain 10 to the main conveying chain 20.

A pressing device is provided above the main conveying chain 20 and configured to press a feces collector during a moving process of the sample box 30.

An image acquisition device, e.g. a camera device 80, is configured to acquire colored information presented on test strips in the sample box 30 on the main conveying chain 20. A detection result may be learned through the colored information. The image acquisition device is provided in the front of a waste discharging device 70.

A major difference of the present invention from the prior art is that a feeding method (a feeding channel) and a detection conveying method (a detection conveying channel) apply the feeding chain 10 and the main conveying chain 20, respectively. Besides, the sample box 30 is clamped by applying the clamping devices 40. Both the feeding channel and the detection and conveying channel apply chain conveying structures. In this way, the clamping devices 40 can well clamp the sample box 30 without affecting conveying, thus matching conveying with clamping organically.

Further, as shown in FIG. 1, the feeding chain 10 and the main conveying chain 20 are located in one horizontal plane, thus facilitating smooth conveying and accurate location of the sample box 30. The clamping devices 40 are installed on laterals of the feeding chain 10 and the main conveying chain 20. The sample box 30 is clamped vertically in the clamping devices 40. The clamping devices 40 do not need to have bottom surfaces. A side face of the sample box 30 is clamped by side faces of the clamping devices 40. In this way, a lateral clamping force and a clamping torque of the clamping devices 40 may be generated for the sample box 30. Such a lateral clamping force and clamping torque can resist an overturning torque of the sample box 30 effectively, thus effectively preventing the sample box 30 from tilting.

Figure 6:
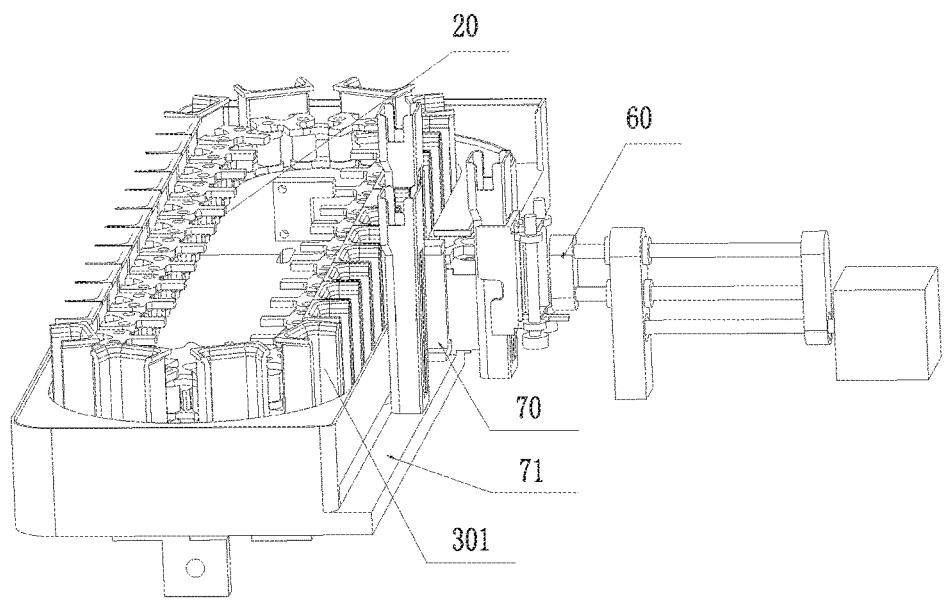
FIG. 6 is a schematic diagram of a working principle of a discharging device.

Further, as shown in FIG. 6, the clamping devices 40 are elastic clamping devices made of elastic materials, and the elastic clamping devices comprise: open slots 301 formed by the elastic materials, openings of the open slots 301 are located in a vertical plane. The openings are lateral ones so as to clamp and output the sample box 30. For example, the open slots 301 are rectangular open slots. The length of the open slots 301 or a clamping length of the clamping devices 40 is a line segment, which can save materials and lighten the weight of whole fecal occult blood detecting analyzer. The length of the open slots 301 or the clamping length of the clamping devices 40 is shorter than the length of the sample box 30, so that the clamping devices 40 are in line contact or plane contact instead of being in point contact with the sample box 30, thus achieving a relatively large contact area to form a stable clamping torque.

Further, the fully automatic fecal occult blood detecting analyzer further comprises a transferring device is used for transferring the sample box 30 from the feeding chain 10 to the main conveying chain 20 so as to transfer the sample box.

Figure 4:
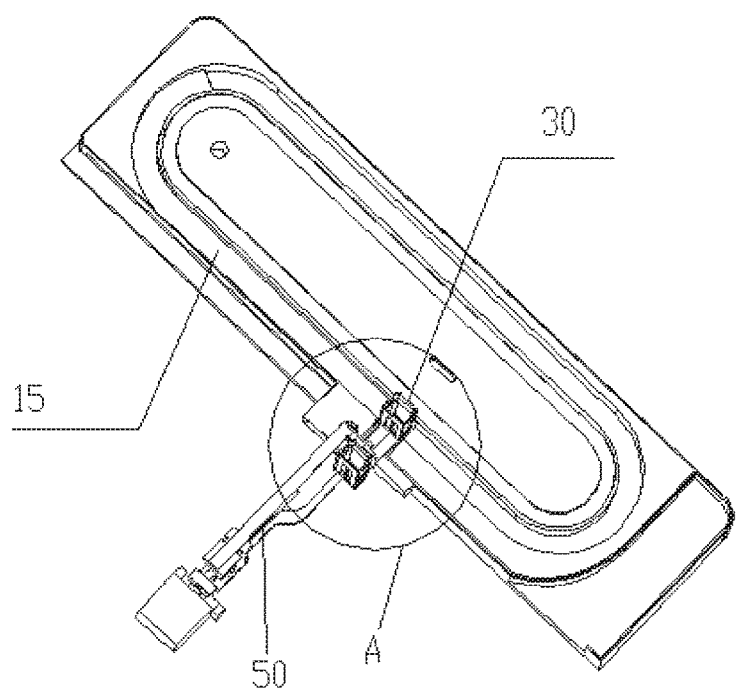
FIG. 4 is a structural schematic diagram of a pull rod according to an embodiment of the present invention.
Figure 5:
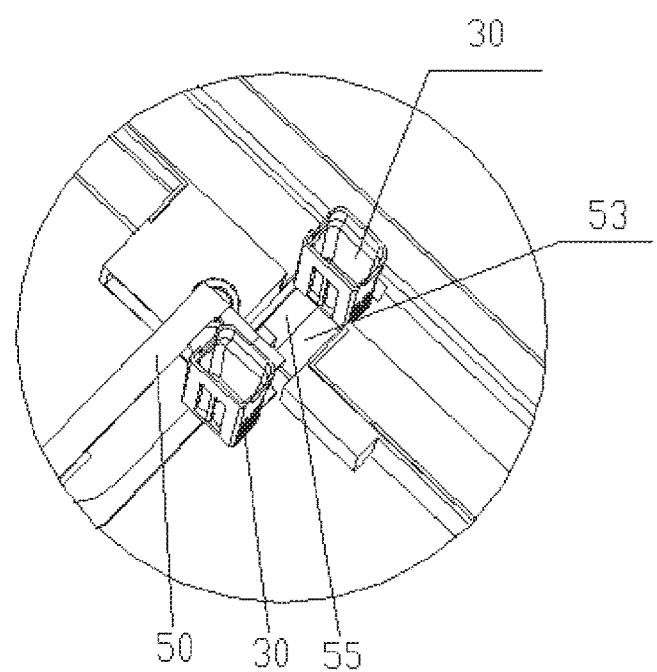
FIG. 5 is an amplified structure of position A in FIG. 4.

Further, as shown in FIG. 4 and FIG. 5, the transferring device comprises: a pull rod 50 is capable of moving between the feeding chain 10 and the main conveying chain 20, and a transferring supporting platform 53 is located between the feeding chain 10 and the main conveying chain 20. The transferring supporting platform 53 supports the sample box 30 during transferring process. The pull rod 50 may be driven by a motor so as to implement a reciprocating motion. Pulled by the pull rod 50 and supported stably by the transferring supporting platform 53, the sample box 30 may be transferred smoothly and rapidly.

Figure 2:
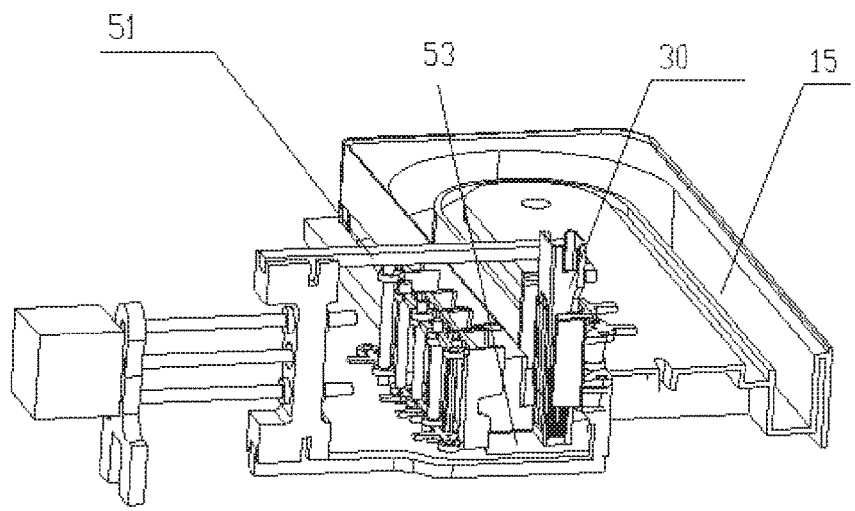
FIG. 2 is a schematic diagram of a working principle of a sample box according to an embodiment of the present invention, wherein the sample box is located on a feeding track and some feeding chains and main conveying chains are removed.
Figure 3:
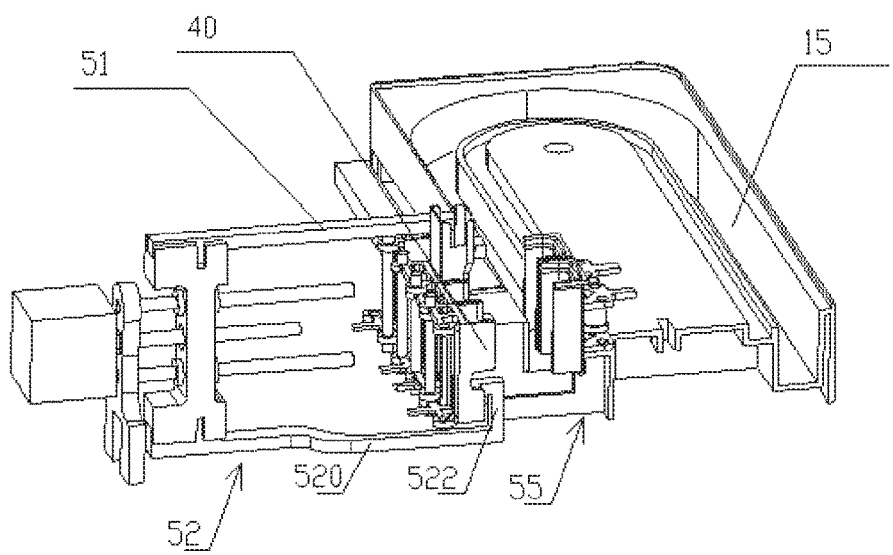
FIG. 3 is a schematic diagram of a working principle of a sample box according to an embodiment of the present invention, wherein the sample box is located on a main conveying track and some feeding chains and main conveying chains are removed.

Further, as shown in FIG. 2 and FIG. 3, the pull rod 50 comprises: an upper pull rod 51 and a lower pull rod 52 located below the upper pull rod 51. The upper pull rod is 51 in a horizontally-provided L shape or in other shapes to hook up the sample box 30. The present invention may be implemented by an upper pull rod 51 in any shapes as long as a plane where upper pull rod 51 locating is higher than the top surfaces of the feeding chain 10 and the main conveying chain 20, thus the upper pull rod 51 is not affected by the feeding chain 10, the main conveying chain 20, a feeding track 15 and a main conveying track during a horizontal reciprocating motion of the upper pull rod 51. The main conveying chain 20 is provided in the main conveying track. The main conveying track is formed by a main conveying chain housing provided with an opening. For example, the main conveying chain housing is manufactured by engineering plastics, a steel plate, engineering aluminum, or a machinable resin plate, and the main conveying chain housing encloses an outer side and the bottom of the main conveying chain 20 to limit the sample box 30 on the main conveying chain 20 in two directions, and supports the bottom of the sample box 30 of the main conveying chain 20 when the pressing device 90 presses the sample box 30 so that the main conveying chain 20 will not be distorted by being pressed, thus avoiding influence on the main conveying chain 20 conveying the sample box 30. Compared with a past conveyor belt, the main conveying track or the main conveying chain housing of the present invention can better maintain a process of conveying the sample box 30 stable during a pressing process, thus avoiding tilting and rollover. The feeding track 15 is formed by a feeding chain housing provided with the opening and the feeding chain housing encloses an outer side and the bottom of the feeding chain 10 so as to limit the sample box 30 on the feeding chain 10 in two directions.

As shown in FIG. 3, the lower pull rod 52 comprises: a horizontally-provided traverse rod 520 and a vertical rod 522 connected to an end of the traverse rod 520. The traverse rod 520 and the vertical rod 522 form an L shape or other shapes in a vertical plane so as to hook up the sample box 30 in the vertical plane. The vertical rod 522 is provided vertically. The traverse rod 520 is lower than the bottom surfaces of the feeding chain 10 and the main conveying chain 20 so as to prevent the traverse rod 520 from being affected by the feeding chain 10 and the main conveying chain 20 during a horizontal motion of the traverse rod 520. The top surface of the vertical rod 522 is lower than a plane where the upper pull rod 51 locating so that the sample box 30 can be pulled at an upper portion and a lower portion, thus avoiding tiling and overturning. An opening 55 for moving the vertical rod 522 is provided in the transferring supporting platform 53. The width of the opening 55 is smaller than that of the sample box 30, thus ensuring that the sample box 30 cannot fall from the opening 55 while supporting the sample box 30. The vertical rod 522 extends from the bottom of the transferring supporting platform 53 or from the opening 55 into the feeding chain 10. The present invention may be implemented by any other shapes of the lower pull rod 52 as long as the foregoing conditions are satisfied. The upper pull rod 51 pulls the sample box 30 in a horizontal plane while the lower pull rod 52 pulls the sample box 30 in a vertical plane, the two pulling planes are vertical to each other, thus the sample box 30 is stressed more reasonably and uniformly when pulled, so as to achieve better effect in preventing overturning. Besides, the sample box 30 can be pulled smoothly at the upper and lower portions, and will not be affected by the main conveying chain 20 and the feeding chain 10. In the meanwhile, the sample box 30 is more stable when pulled by the supporting function of the transferring supporting platform 53. In addition, the structure is compact and can be installed in a relatively small space conveniently, especially in the machine shell 104 as shown in FIG. 7 and FIG. 8. Of course, an upper pull rod 51 and a lower pull rod 52 of other shapes are also feasible, as long as the foregoing conditions are satisfied and the upper pull rod 51 and the lower pull rod 52 can be installed in the machine shell 104.

Further, as shown in FIG. 1 and FIG. 6, the fully automatic fecal occult blood detecting analyzer further comprises: a discharging device 60 is used for sending the sample box 30 out from the main conveying chain 20. The discharging device 60 is a device capable of reciprocating, such as a push block or a push rod component and so on. The discharging device 60 may be driven by a motor to push the sample box 30 from the clamping devices 40 on the main conveying chain 20 in a vertical direction relative to the main conveying chain 20.

Further, as shown in FIG. 6, the fully automatic fecal occult blood detecting analyzer further comprises: a waste supporting platform 71 is used for supporting the sample box 30 sent out by the discharging device 60. The waste supporting platform 71 is located between the feeding chain 10 and the main conveying chain 20, and the waste supporting platform 71 and the transferring supporting platform 53 are located on the same plane, thus connecting feeding and discharging smoothly. Besides, the longitudinal width of the waste supporting platform 71 is smaller than the length of a long side of the sample box 30, thus preventing the sample box 30 from rotating when being sent out.

Further, as shown in FIG. 6, the fully automatic fecal occult blood detecting analyzer further comprises: a waste discharging device 70 is used for pushing the sample box 30 away from the waste supporting platform 71 in a horizontal direction relative to the main conveying chain 20, so that the waste supporting platform 71 may be cleared in time and a detected sample box 30 may be discharged, thus ensuring detection continuity. The waste discharging device 70 is a moveable component, such a device capable of reciprocating as a push block or a push rod component and so on. The sample box is supported by the waste supporting platform 71 during a discharging process and will not fall down. It doesn't matter even if the sample box 30 falls down, because the sample box 30 is sealed during the whole process, thus avoiding pollution to the detecting analyzer and the environment.

Further, the fully automatic fecal occult blood detecting analyzer further comprises: a stepping motor is used for driving the feeding chain 10 to move and vibrating the sample box 30. The feeding chain 10 is moved by rotation of the driving wheel of the feeding chain 11, and the driving wheel of the feeding chain 11 is connected to the stepping motor. The stepping motor not only plays a driving function, but also generates vibration through regulating a rotating speed of the stepping motor to shake the feces collector, thus mixing a fecal sample and a diluent. Labour is saved and efficiency is improved during a process in which manual shaking is unnecessary. As shown in FIG. 1, the fully automatic fecal occult blood detecting analyzer further comprises: the pressing device 90 is configured to press an upper cover of the feces collector in the sample box 30 to pierce an easy tear material at a lower end of the feces collector. The test strips start to react and change colors. When the pressing device 90 presses the sample box, the bottom of the main conveying track is a platform with a certain height from the main conveying chain so as to support the sample box 30.

As shown in FIG. 7 and FIG. 8, the fully automatic fecal occult blood detecting analyzer further comprises: the machine shell 104 for accommodating components comprising a housing of the feeding chain, a main conveying chain housing, the driving wheel of the feeding chain 11, the driving wheel of the main conveying chain 21, the clamping devices 40, and various sensors, and so on. A feed inlet port 101 is provided on the machine shell 104. The feed inlet port 101 communicates with the feeding chain 10 and is used for feeding the sample box to the feeding chain 10, i.e. is used for adding a to-be-detected sample box. By using the machine shell 104, internal components can be protected and moved integrally, thus facilitating moving.

The fully automatic fecal occult blood detecting analyzer further comprises: a discharging port 105 is provided on the machine shell 104, the discharging port 105 is used for pushing the sample box 30 from the waste supporting platform 71 to leave the fully automatic fecal occult blood detecting analyzer therefrom. The machine shell 104 of the detecting analyzer is provided with a protection cover 102 at the feed inlet port 101. The protection cover thereon is provided with a sensing device capable of stopping the feeding chain from moving when a tester opens the protection cover to feed a sample box, thus protecting the tester. The main conveying chain, which will not stop working, is able to continue subsequent image acquisition and discharging action.

Preferably, the fully automatic fecal occult blood detecting analyzer further comprises: an information processing unit signally communicates with the barcode scanning device 88 and the image acquisition device, which is not shown in the figures, a printing device 107 is provided on the machine shell, and a control panel 109 is provided thereon. The barcode scanning device 88 reads information of a barcode. The image acquisition device acquires colored strip information presented on the test strips in the sample box on the main conveying chain, and the colored strip information is processed by the information processing unit to generate a detection result which is printed by the printing device 107 or displayed by the control panel 109. The barcode scanning device 88 may be located at an appropriate position of the whole analyzer to acquire barcode information on the feces collector in the sample box 30.

Preferably, the fully automatic fecal occult blood detecting analyzer further comprises: a recycling device is located at a terminal end of the waste supporting platform 71 and configured to recycle the sample box 30, which is not shown in the figures, thus preventing the sample box 30 from being discharged randomly and avoiding environmental pollution.

Preferably, the fully automatic fecal occult blood detecting analyzer further comprises: the machine shell 104 is configured to enclose the feeding chain 10, the main conveying chain 20, the driving wheel of the feeding chain 11, the driving wheel of the main conveying chain 21 and the clamping devices 40.

Preferably, the fully automatic fecal occult blood detecting analyzer further comprises: the feed inlet port 101 is provided on the machine shell 104 and communicating with the feeding chain 10.

Preferably, the fully automatic fecal occult blood detecting analyzer further comprises: the protection cover 102 is provided on the machine shell 104 and located at the feed inlet port 101.

Preferably, the fully automatic fecal occult blood detecting analyzer further comprises: a flange is provided at one or two sides of the machine shell 104 above the waste supporting platform 71, which is not shown in the figure. The flange can implement line and plane contact with a discharged sample box 30, thus preventing the sample box 30 from rotating when discharged.

In the present invention, the machine shell 104 therein is provided with a first sensor 81 for sensing a position of the sample box 30 in the feeding chain 10, so as to protect feeding and prevent hands from being clamped. The machine shell 104 therein is provided with a second sensor 82 for detecting a position of the sample box 30 in the main conveying chain 20 and determining whether transferring action is performed or whether the pull rod 50 acts. The machine shell 104 therein is provided with a third sensor 83 for detecting a position of the sample box 30 in the main conveying chain 20 when the pressing device 90 presses. The machine shell 104 therein is provided with a fourth sensor 84 for detecting a position of the sample box 30 in the main conveying chain 20 during a photographing process. The machine shell 104 therein is provided with a fifth sensor 85 for detecting a position of the sample box 30 in the main conveying chain 20 during a discharging process. The transferring device is inside the feeding chain 10 before the sample box arrives, that is, the transferring device has extended into the feeding chain 10. After the sample box 30 is transferred to the main conveying chain 20, the transferring device needs to return into the feeding chain 10 again. At the moment, a sensing device, i.e. the second sensor 82 senses acquires a state, the feeding chain 10 stops moving, the transferring device returns into the feeding chain 10 again, and the feeding chain 10 is restarted.

After a fecal sample of a patient is collected, the fecal sample is sealed in the feces collector of the sample box 30. During detection, the feces collector is pressed at a sealed state and is pierced by a spike located below the feces collector at the bottom of the sample box 30 so that a diluent of the fecal sample flows out. Besides, the feces collector always performs conveyance under the cooperation of the clamping devices 40, thus more effectively preventing the diluent with the fecal sample in the feces collector from flowing out. In addition, the sample box 30 is fully sealed to avoid pollution to a surrounding environment. The detecting analyzer does not need a mechanic probe in the prior art to suck up and add droplets of a sample thus there is no risk of cross infection. In the meanwhile, the detecting analyzer does not need to perform shaking manually, because the stepping motor will generate vibration at an excessively low rotating speed, thus mixing the fecal sample and the diluent. The detecting analyzers can complete detection automatically and generate a detection result, thus the detection efficiency is greatly improved. In addition, a doctor can get rid of a manual detection method, thus improving the sensory comfort of the doctor.

The present invention can implement continuous detection and accurate location of a plurality of sample boxes. The sample boxes will not be overturned, tilted and so on, and can be pressed accurately, and diluents of fecal samples react with test strips so as to complete detection. In the meanwhile, the detecting analyzer shakes a sample box by using a disadvantage of the stepping motor that vibration will be generated at an excessively low rotating speed, thus saving labour and improving efficiency. The analyzer is provided with the protection cover. When the protection cover is opened to feed, the feeding chain is stopped, thus protecting a tester and preventing hands from being clamped. At the same time, the whole machine, which occupies a small area, can be controlled by a Programmable Logic Controller (PLC) and may be also controlled by an integrated circuit board. The feeding chain and the main conveying chain moves independently without influencing each other. Each component works in a streamlined manner, thus implementing continuous detection and improving detection efficiency. The speed of the main conveying chain is controllable and adjustable, and the time between a moment when a sample box is pressed and a moment when a detection result is acquired through an image acquisition device is accurate.

The foregoing descriptions are merely specific schematic embodiments of the present invention, and are by no means intended to limit the scope thereof. All components of the present invention may be combined with each other if there is no conflict. Equivalent changes and modifications made by those skilled in the art without departing from the concept and principles of the present invention should fall within the scope of protection of the present invention.

What is claimed is:

1. A fully automatic fecal occult blood detecting analyzer used to detect a sample box, wherein the sample box comprises a transparent sleeve, a feces collector and test strips provided in the transparent sleeve, the fully automatic fecal occult blood detecting analyzer comprising:
    a feeding chain and a main conveying chain;
    a plurality of clamping devices for clamping the sample boxes, provided on the feeding chain and the main conveying chain, respectively;
    a transferring device provided between the feeding chain and the main conveying chain;
    a pressing device configured to press the feces collector during a moving process of the sample box and provided above the main conveying chain; and
    an image acquisition device configured to acquire colored tape information presented on the test strips in the sample box on the main conveying chain.

2. The fully automatic fecal occult blood detecting analyzer according to claim 1,
    wherein both the feeding chain and the main conveying chain are located in one horizontal plane;
    wherein the clamping devices are installed on outer circumferences of the feeding chain and the main conveying chain;
    wherein the sample box is clamped vertically in the clamping devices; and
    wherein a side face of the sample box is clamped by side faces of the clamping devices.

3. The fully automatic fecal occult blood detecting analyzer according to claim 2,
    wherein the clamping devices are elastic clamping devices made of elastic materials, and
    wherein the elastic clamping devices comprise: open slots formed by the elastic material, and wherein the open slots are located in a vertical plane of the elastic clamping devices.

4. The fully automatic fecal occult blood detecting analyzer according to claim 1, wherein the transferring device comprises:
   a pull rod moving between the feeding chain and the main conveying chain, and
   a transferring supporting platform located between the feeding chain and the main conveying chain;
   wherein the transferring supporting platform supports the sample box.

5. The fully automatic fecal occult blood detecting analyzer according to claim 4,
   wherein the pull rod comprises: an upper pull rod and a lower pull rod located below the upper pull rod;
   wherein a plane where the upper pull rod is located is higher than top surfaces of the feeding chain and the main conveying chain;
   wherein the lower pull rod comprises: a horizontal rod and a vertical rod connected to an end of the traverse rod;
   wherein the horizontal rod is lower than bottom surfaces of the feeding chain and the main conveying chain;
   wherein a top surface of the vertical rod is lower than the plane where the upper pull rod is located;
   wherein an opening is provided in the transferring supporting platform;
   wherein a width of the opening is smaller than that of the sample box; and
   wherein the lower pull rod extends from a bottom of the transferring supporting platform into the feeding chain.

6. The fully automatic fecal occult blood detecting analyzer according to claim 5, wherein the fully automatic fecal occult blood detecting analyzer further comprises: a discharging device used for sending the sample box out from the main conveying chain.

7. The fully automatic fecal occult blood detecting analyzer according to claim 6,
   wherein the fully automatic fecal occult blood detecting analyzer further comprises: a waste supporting platform used for supporting the sample box sent out by the discharging device;
   wherein the waste supporting platform is located between the feeding chain and the main conveying chain, and the waste supporting platform and the transferring supporting platform are located on a same plane; and
   wherein a longitudinal width of the waste supporting platform is smaller than the length of a long side of the sample box.

8. The fully automatic fecal occult blood detecting analyzer according to claim 7, wherein the fully automatic fecal occult blood detecting analyzer further comprises: a waste discharging device for pushing the sample box away from the waste supporting platform.

9. The fully automatic fecal occult blood detecting analyzer according to claim 7, wherein the fully automatic fecal occult blood detecting analyzer further comprises:
   a machine shell configured to enclose the feeding chain, the main conveying chain, a driving wheel of the feeding chain, a driving wheel of the main conveying chain, and the clamping devices;
   a feed inlet port provided on the machine shell and communicating with the feeding chain;
   a protection cover provided on the machine shell and located at the feed inlet port; and
   a flange provided at one or two sides of the machine shell above the waste supporting platform.

10. The fully automatic fecal occult blood detecting analyzer according to claim 1, wherein the fully automatic fecal occult blood detecting analyzer further comprises a stepping motor for driving the feeding chain to move and vibrating the sample box.

* * * * *